(12) United States Patent
Lin et al.

(10) Patent No.: US 10,704,051 B2
(45) Date of Patent: Jul. 7, 2020

(54) EXPRESSION ELEMENT, EXPRESSION CASSETTE, AND VECTOR CONTAINING THE SAME

(71) Applicant: Agricultural Technology Research Institute, Hsinchu (TW)

(72) Inventors: Jiunn-Horng Lin, Hsinchu (TW); Jyh-Perng Wang, Hsinchu (TW); Zeng-Weng Chen, Hsinchu (TW); Chien-Yu Fang, Hsinchu (TW); Hao-Zhen Zeng, Hsinchu (TW); Jian-Fong Lai, Hsinchu (TW); Weng-Zeng Huang, Hsinchu (TW); Shih-Ling Hsuan, Hsinchu (TW)

(73) Assignee: AGRICULTURAL TECHNOLOGY RESEARCH INSTITUTE, Hsinchu (TW)

( * ) Notice: Subject to any disclaimer, the term of this patent is extended or adjusted under 35 U.S.C. 154(b) by 357 days.

(21) Appl. No.: 15/520,680

(22) PCT Filed: Dec. 29, 2014

(86) PCT No.: PCT/CN2014/095340
§ 371 (c)(1),
(2) Date: Apr. 20, 2017

(87) PCT Pub. No.: WO2016/106504
PCT Pub. Date: Jul. 7, 2016

(65) Prior Publication Data
US 2018/0216119 A1    Aug. 2, 2018

(51) Int. Cl.
*C12N 15/67* (2006.01)
*C12N 15/70* (2006.01)
*C12N 15/63* (2006.01)

(52) U.S. Cl.
CPC ............ *C12N 15/67* (2013.01); *C12N 15/63* (2013.01); *C12N 15/70* (2013.01); *C12N 2840/002* (2013.01)

(58) Field of Classification Search
CPC ................................ C12N 15/67; C12N 15/70
See application file for complete search history.

(56) References Cited

U.S. PATENT DOCUMENTS

| 5,017,493 | A | 5/1991 | Andersen et al. |
| 6,610,533 | B1 * | 8/2003 | Inouye ................. C07K 14/245 |
|  |  |  | 435/320.1 |
| 6,737,245 | B1 * | 5/2004 | Francis ................. C12N 15/74 |
|  |  |  | 435/189 |
| 2005/0272924 | A1 | 12/2005 | Inouye et al. |
| 2006/0292671 | A1 | 12/2006 | Schneider et al. |

FOREIGN PATENT DOCUMENTS

| CN | 1242427 A | 1/2000 |
| CN | 1639320 A | 7/2005 |
| CN | 1873000 A | 12/2006 |
| CN | 101193906 A | 6/2008 |

OTHER PUBLICATIONS

CN 1873000 A translation, accessed Aug. 30, 2019, pp. 1-17 (Year: 2019).*
International Search Report for PCT/CN2014/095340 (PCT/ISA/210) dated Sep. 14, 2015.

* cited by examiner

*Primary Examiner* — Antonio Galisteo Gonzalez
(74) *Attorney, Agent, or Firm* — Birch, Stewart, Kolasch & Birch, LLP

(57) ABSTRACT

The present invention provides an expression element and an expression cassette to establish a novel vector therefrom. The expression element of the present invention has an effect of enhancing the expression level of the target gene so that is highly industrial valuable. Accordingly, the present vector is taken as a novel tool for genetic engineering.

16 Claims, 2 Drawing Sheets
Specification includes a Sequence Listing.

| Expression elements | Modified region | DNA sequences |
|---|---|---|
| araB-W | none | -35　　　　　　　　　　　　　　　　-10　　　　　　　　　　　　　　　　　　SD　　　　　Start Codon<br>GGATCCTACCTGACGCTTTTTATCGCAACTCTCTACTGTTTCTCCATACCCGTTTTTTGGAT[GGAGTG]AACATATG<br>(SEQ ID NO: 47) |
| araB-M1 | SD | -35　　　　　　　　　　　　　　　　-10　　　　　　　　　　　　　　　　　　SD　　　　　Start Codon<br>GGATCCTACCTGACGCTTTTTATCGCAACTCTCTACTGTTTCTCCATACCCGTTTTTTGGAT[TAAGGAGG]ATACATATG<br>(SEQ ID NO: 13) |
| araB-M2 | SD | -35　　　　　　　　　　　　　　　　-10　　　　　　　　　　　　　　　　　　SD　　　　　Start Codon<br>GGATCCTACCTGACGCTTTTTATCGCAACTCTCTACTGTTTCTCCATACCCGTTTTTTGGATA[AGGAGG]ATACATATG<br>(SEQ ID NO: 14) |
| araB-M3 | SD | -35　　　　　　　　　　　　　　　　-10　　　　　　　　　　　　　　　　　　SD　　　　　Start Codon<br>GGATCCTACCTGACGCTTTTTATCGCAACTCTCTACTGTTTCTCCATACCCGTTTTTTGGATAT[AGGAGGT]ATACATATG<br>(SEQ ID NO: 15) |
| araB-M4 | SD | -35　　　　　　　　　　　　　　　　-10　　　　　　　　　　　　　　　　　　SD　　　　　Start Codon<br>GGATCCTACCTGACGCTTTTTATCGCAACTCTCTACTGTTTCTCCATACCCGTTTTTTGGATAT[AGGAGG]AATACATATG<br>(SEQ ID NO: 16) |
| araB-M5 | SD | -35　　　　　　　　　　　　　　　　-10　　　　　　　　　　　　　　　　　　SD　　　　　Start Codon<br>GGATCCTACCTGACGCTTTTTATCGCAACTCTCTACTGTTTCTCCATACCCGTTTTTTGGATGA[AGGAG]AATACATATG<br>(SEQ ID NO: 17) |
| araB-M6 | -10 & SD | -35　　　　　　　　　　　　　　　　-10　　　　　　　　　　　　　　　　　　SD　　　　　Start Codon<br>GGATCCTACCTGACGCTTTTTATCGCAACTCTCTATAAATTCTCCATACCCGTTTTTTGGATAT[AGGAGG]AATACATATG<br>(SEQ ID NO: 18) |
| araB-M7 | -16 & SD | -35　　　　　　　　　　　-16　　-10　　　　　　　　　　　　　　　　　　SD　　　　　Start Codon<br>GGATCCTACCTGACGCTTTTTATCGCAACTTGCTACTGTTTCTCCATACCCGTTTTTTGGATAT[AGGAGG]AATACATATG<br>(SEQ ID NO: 19) |
| araB-M10 | T7 epsilon & SD | -35　　　　　　　　　　　　　　　　-10　　　　　　　　　　　　　　　　T7 epsilon　　　SD　　　　Start Codon<br>GGATCCTACCTGACGCTTTTTATCGCAACTCTCTACTGTTTCTCCATACCCGTTTTTTG[TTAACTTTA]AGA[AGGAGG]AATACATATG<br>(SEQ ID NO: 20) |
| araB-M11 | -16 & T7 epsilon & SD | -35　　　　　　　　　　　-16　　-10　　　　　　　　　　　　　　　　　T7 epsilon　　　SD　　　　Start Codon<br>GGATCCTACCTGACGCTTTTTATCGCAACTTGCTACTGTTTCTCCATACCCGTTTTTTG[TTAACTTTA]AGA[AGGAGG]AATACATATG<br>(SEQ ID NO: 21) |

FIG. 1

| Expression elements | Modified region | DNA sequences |
|---|---|---|
| araB-M7-DS1 | -16 & SD & DS1 | GGATCCTACCTGACGCTTTTTATCGCAACTTGCTACTGTTCTCCATACCCGTTTTTTGGATAT\|AGGAGG\|AATACATATGCACACACACACACACACACTCA (SEQ ID NO: 22) |
| araB-M7-DS2 | -16 & SD & DS2 | GGATCCTACCTGACGCTTTTTATCGCAACTTGCTACTGTTCTCCATACCCGTTTTTTGGATAT\|AGGAGG\|AATACATATGAAAGCAATTTTCGTA (SEQ ID NO: 23) |
| araB-M7-DS4 | -16 & SD & DS4 | GGATCCTACCTGACGCTTTTTATCGCAACTTGCTACTGTTCTCCATACCCGTTTTTTGGATAT\|AGGAGG\|AATACATATGAATCACAAAGTG (SEQ ID NO: 24) |
| araB-M7-DS5 | -16 & SD & DS5 | GGATCCTACCTGACGCTTTTTATCGCAACTTGCTACTGTTCTCCATACCCGTTTTTTGGATAT\|AGGAGG\|AATACATATGACTAGCAAAAGA (SEQ ID NO: 25) |
| araB-M11-DS1 | -16 & T7 epsilon & SD & DS1 | GGATCCTACCTGACGCTTTTTATCGCAACTTGCTACTGTTCTCCATACCCGTTTTTTG\|TTAACTTTA\|AGA\|AGGAGG\|AATACATATGCACACACACACACACACACTCA (SEQ ID NO: 26) |
| araB-M11-DS2 | -16 & T7 epsilon & SD & DS2 | GGATCCTACCTGACGCTTTTTATCGCAACTTGCTACTGTTCTCCATACCCGTTTTTTG\|TTAACTTTA\|AGA\|AGGAGG\|AATACATATGAAAGCAATTTTCGTA (SEQ ID NO: 27) |
| araB-M11-DS4 | -16 & T7 epsilon & SD & DS4 | GGATCCTACCTGACGCTTTTTATCGCAACTTGCTACTGTTCTCCATACCCGTTTTTTG\|TTAACTTTA\|AGA\|AGGAGG\|AATACATATGAATCACAAAGTG (SEQ ID NO: 28) |
| araB-M11-DS5 | -16 & T7 epsilon & SD & DS5 | GGATCCTACCTGACGCTTTTTATCGCAACTTGCTACTGTTCTCCATACCCGTTTTTTG\|TTAACTTTA\|AGA\|AGGAGG\|AATACATATGACTAGCAAAAGA (SEQ ID NO: 29) |

FIG. 1 (cont.)

EXPRESSION ELEMENT, EXPRESSION CASSETTE, AND VECTOR CONTAINING THE SAME

REFERENCE TO SEQUENCE LISTING SUBMITTED VIA EFS-WEB

This application includes an electronically submitted sequence listing in .txt format. The .txt file contains a sequence listing entitled "2017-09-18_5025-0267PUS1_ST25.txt" created on Sep. 18, 2017 and is 10,640 bytes in size. The sequence listing contained in this .txt file is part of the specification and is hereby incorporated by reference herein in its entirety.

BACKGROUND OF THE INVENTION

Field of the Invention

The present invention relates to an expression element, especially an expression element of an arabinose-inducible expression system.

Description of the Prior Art

An expression system is composed of host cells and genetic elements, such as transcription and translation signals, regulatory factors, genes, and plasmids. A variety of eukaryotic and prokaryotic expression systems have been established and even commercialized.

Research results and development experience of *Escherichia coli* expression system are the most abundant among expression systems. Techniques for gene manipulation and fermentation related to *E. coli* expression system have developed very well. The advantages of producing recombinant proteins with *E. coli* include that genes can be easily manipulated, incubation of *E. coli* is easy, *E. coli* grows fast and can be incubated to a high density in cheap medium, expression vectors and improved hosts, such as protease deficient strain, have many options, protein expression level is high, and the production time is short.

There have been a variety of *E. coli* expression systems available, such as trc expression system, T7 expression system, and pBAD expression system. Among these expression systems, pBAD expression system is an arabinose-inducible expression system, which consists of arabinose-inducible expression elements, expression vectors regulating gene expression, and *E. coli* host cells. The advantages of this expression system are (1) being able to tightly regulate gene expression to avoid toxicity caused by gene expression leakage; (2) lower costs because of using arabinose as the inducer; and (3) being able to control protein expression level with different arabinose concentrations.

In light of the above-mentioned advantages of the arabinose-inducible expression system, there is a need to develop better expression elements for both research and commercial purposes.

SUMMARY OF THE INVENTION

Hence, one object of the present invention is to provide expression elements and an expression cassette containing thereof. The expression elements above can enhance the expression level of a gene to be expressed, and, therefore, the expression elements are more valuable for industrial application.

Another object of the present invention is to provide a vector, which comprises the expression cassette above and is used for the arabinose-inducible expression system. Therefore, a novel option for application of the arabinose-inducible expression system is provided for the field of the invention.

In order to achieve the foregoing objects, the present invention provides an expression element of an arabinose-inducible expression system, which comprises: a promoter and at least one of the following elements: a ribosome binding site having a sequence of SEQ ID NO: 01; or a bacteriophage T7 epsilon enhancer element having a sequence of SEQ ID NO: 08.

The present invention also provides an expression cassette, which comprises: an above-mentioned expression element, a start codon, a gene to be expressed, and a stop codon.

The present invention further provides a vector, which comprises: an above-mentioned expression cassette and a multiple cloning site.

Preferably, −10 region of the promoter has a sequence of SEQ ID NO: 06.

Preferably, −16 region of the promoter has a sequence of SEQ ID NO: 07.

Preferably, the ribosome binding site has a sequence of SEQ ID NO: 02, SEQ ID NO: 03, SEQ ID NO: 04, SEQ ID NO: 05, or a combination thereof.

Preferably, the expression element has a sequence of SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, or a combination thereof.

Preferably, a downstream sequence is disposed between the start codon and the gene to be expressed, and the downstream sequence has a sequence of SEQ ID NO: 09, SEQ ID NO: 10, SEQ ID NO: 11, SEQ ID NO: 12, or a combination thereof.

Preferably, the expression cassette further comprises a regulatory gene. Preferably, the regulatory gene is regulatory gene araC of arabinose-inducible expression.

Preferably, the gene to be expressed is: a gene translated into a green fluorescent protein, a gene of an enzyme, a gene of an antigen, a gene of a peptide and a protein having physiological activity, or a combination thereof.

Preferably, the vector further comprises a replication start site, a selectable marker, a signal peptide, or a combination thereof.

Preferably, the selectable marker contained in the vector is: a drug resistance selectable marker, a non-drug resistance selectable marker, or a combination thereof.

In summary, the present invention provides an expression element and an expression cassette of an arabinose-inducible expression system to construct a vector. The vector can be used for the expression of a gene of interestby an *E. coli* system and has efficacy to enhance the expression level of the gene to be expressed. Accordingly, the present invention provides a novel expression vector as an alternative novel option in the field of genetic engineering.

BRIEF DESCRIPTION OF THE DRAWINGS

FIG. 1 shows the comparison of sequences of each expression element in the examples of the present invention.

DETAILED DESCRIPTION OF THE EMBODIMENTS

In light of the advantages of the arabinose-inducible expression system in gene engineering, the present invention is intended to provide an expression element, which is used for the arabinose-inducible expression system and helps to enhance the expression level of a gene to be expressed. By using the expression element of the present invention, the conventional arabinose expression system can be of greater industrial value.

One aspect of the present invention is to provide an expression element. The expression element comprises a promoter and at least one of the following elements: a ribosome binding site or a bacteriophage T7 epsilon enhancer element.

The term "expression element" as used herein refers to the nucleotide sequence associated with gene expression at the upstream of the start codon. In a feasible embodiment, the expression element includes: a promoter (including −10 region, −16 region, and/or −35 region), a ribosome binding site, a regulatory sequence for gene expression, or a combination thereof.

In an alternative embodiment, there is no need to limit the types of the promoters. A person having ordinary skill in the art can select a suitable promoter for their needs. In a preferable embodiment, the "promoter" is the promoter of araB gene, which allows the expression element suitable for an arabinose-inducible expression system. In a preferable embodiment, −10 region of the promoter has a sequence of SEQ ID NO: 06. In another preferable embodiment, −16 region of the promoter contained in the expression element has a sequence of SEQ ID NO: 07.

The term "ribosome binding site" as used herein refers to a sequence which can be recognized and bound by ribosomes during the translation process. In a preferable embodiment, the ribosome biding site has a sequence of SEQ ID NO: 01. In a feasible embodiment, the ribosome biding site has a sequence of SEQ ID NO: 02, SEQ ID NO: 03, SEQ ID NO: 04, SEQ ID NO: 05, or a combination thereof. The term "bacteriophage T7 epsilon enhancer element" as used herein refers to the nucleotide sequence at upstream of the start codon of gene 10 of bacteriophage T7. In a feasible embodiment, the bacteriophage T7 epsilon enhancer element has a sequence of SEQ ID NO: 08.

Another aspect of the present invention is to provide an expression cassette, which comprises the above-mentioned expression element, a start codon, a gene to be expressed, and a stop codon. In a preferable embodiment, a downstream sequence is disposed between the start codon and the gene to be expressed, and the downstream sequence has a sequence of SEQ ID NO: 09, SEQ ID NO: 10, SEQ ID NO: 11, SEQ ID NO: 12, or a combination thereof. In a preferable embodiment, the expression cassette further comprises a regulatory gene.

The term "regulatory gene" as used herein refers to a DNA sequence which can translate a regulatory protein for control of gene expression. In a feasible embodiment, the regulatory gene is araC.

The term "a gene to be expressed" as described herein may vary for the needs of a user. The gene to be expressed is, for example, but not limited to, a gene encoding a green fluorescent protein, a gene encoding an enzyme, a gene encoding an antigen, a gene encoding a peptide or a protein having physiological activity, or a combination thereof. The term "start codon" described herein refers to the codon of an mRNA that starts to be translated. In a feasible embodiment, the start codon is ATG. The term "stop codon" described herein refers to the codon that stops the translation. In a feasible embodiment, the stop codon is TAA, TAG, or TGA.

Another aspect of the present invention is to provide a vector, which comprises the above-mentioned expression cassette and a multiple cloning site. In a preferable embodiment, the vector further comprises a replication start site, a selectable marker, a signal peptide, or a combination thereof.

In a feasible embodiment, the multiple cloning site comprises at least one nucleotide sequence that can be recognized by a restriction enzyme. The restriction enzyme includes but not limited to: BamHI, BglII, EcoRI, HindIII, NdeI, PstI, SalI, SpeI, XbaI, XhoI, XmaI, or a combination thereof.

The term "a selectable marker" as used herein is used to confirm whether the above-mentioned vector is successfully transformed into a host. The selectable marker is, but not limited to, a drug resistance selectable marker, a non-drug resistance selectable marker, or a combination thereof.

The term "a drug resistance selectable marker" as used herein means that the transformation of a vector into the host is confirmed by the antibiotic resistance of transformants. For example, the drug resistance selectable marker is a tetracycline resistance gene. In this feasible embodiment, hosts (such as $E.\ coli$) that are successfully transformed with the vector will have resistance to tetracycline and survive in an environment containing tetracycline.

The term "a non-drug resistance selectable marker" as used herein means that the transformation of a vector into host is not confirmed by the antibiotic resistance of transformants. The non-drug resistance selectable marker is, for example, but not limited to, the nucleic acid sequence of β-galactosidase. In the embodiment in which the nucleic acid sequence of β-galactosidase is used as a selectable marker, host cells with successful transformation can cleave X-gal (5-bromo-4-chloro-3-indolyl-β-D-galactopyranoside) into galactose and 5-bromo-4-chloro-3-hydroxyindole. The latter then spontaneously dimerizes into 5,5'-dibromo-4,4'-dichloro-indigo, which is an insoluble, identifiable blue substance.

In a preferable embodiment, the non-drug resistance selectable marker is a complementary gene of an auxotrophic mutation, (such as thymidylate synthase gene, amino acid synthesis related genes, carbohydrate synthesis related genes, and nicotinamide adenine dinucleotide synthesis related genes) and fatty acid synthesis gene fabI.

Example 1: Construction and Transformation of the Arabinose-Inducible Expression Vector of the Present Invention In this example, the expression elements of the original arabinose-inducible expression system were obtained, and −10 region of the promoter, −16 region of the promoter, and the ribosomal binding site (Shine-Dalgarno sequence; SD) were modified, or an additional bacteriophage T7 epsilon enhancer sequence (T7) and/or a downstream sequence were added. The above-mentioned expression element was then inserted to pRPSJ-GFPT, pARABM7-GFPT, or pARABM11-GFPT to form the expression vectors of the present invention. Finally, the enhanced green fluorescent protein gene was used as a reporter gene, and the gene was expressed through the $E.\ coli$ expression system. The expression elements obtained in this example are shown in Table 1 below:

TABLE 1

The expression elements obtained in this example.

| Name | -10 | -16 | SD | T7 | Downstream sequence |
|---|---|---|---|---|---|
| araB-M1 (SEQ ID NO: 13) | -TACTGT- | -CT- | NO: 05 | None | None |
| araB-M2 (SEQ ID NO: 14) | -TACTGT- | -CT- | NO: 04 | None | None |
| araB-M3 (SEQ ID NO: 15) | -TACTGT- | -CT- | NO: 03 | None | None |
| araB-M4 (SEQ ID NO: 16) | -TACTGT- | -CT- | NO: 02 | None | None |
| araB-M5 (SEQ ID NO: 17) | -TACTGT- | -CT- | NO: 01 | None | None |
| araB-M6 (SEQ ID NO: 18) | NO: 10 | -CT- | NO: 02 | None | None |
| araB-M7 (SEQ ID NO: 19) | -TACTGT- | NO: 07 | NO: 02 | None | None |
| araB-M10 (SEQ ID NO: 20) | -TACTGT- | CT | NO: 02 | NO: 08 | None |
| araB-M11 (SEQ ID NO: 21) | -TACTGT- | NO: 07 | NO: 02 | NO: 08 | None |
| araB-M7-DS1 (SEQ ID NO: 22) | -TACTGT- | NO: 07 | NO: 02 | None | NO: 09 |
| araB-M7-DS2 (SEQ ID NO: 23) | -TACTGT- | NO: 07 | NO: 02 | None | NO: 10 |
| araB-M7-DS4 (SEQ ID NO: 24) | -TACTGT- | NO: 07 | NO: 02 | None | NO: 11 |
| araB-M7-DS5 (SEQ ID NO: 25) | -TACTGT- | NO: 07 | NO: 02 | None | NO: 12 |
| araB-M11-DS1 (SEQ ID NO: 26) | -TACTGT- | NO: 07 | NO: 02 | NO: 08 | NO: 09 |
| araB-M11-DS2 (SEQ ID NO: 27) | -TACTGT- | NO: 07 | NO: 02 | NO: 08 | NO: 10 |
| araB-M11-DS4 (SEQ ID NO: 28) | -TACTGT- | NO: 07 | NO: 02 | NO: 08 | NO: 11 |
| araB-M11-DS5 (SEQ ID NO: 29) | -TACTGT- | NO: 07 | NO: 02 | NO: 08 | NO: 12 |

-10: -10 region of the promoter.
-16: -16 region of the promoter.
SD: ribosome binding site.
T7: bacteriophage T7 epsilon enhancer sequence.
No.*: SEQ ID NO.*
-**-: nucleotide sequence.

The construction of the various arabinose-inducible expression vectors of this example is shown as follows:

1. Construction of the Original Arabinose-Inducible Expression Vector

The amplification of the original arabinose-inducible expression elements was performed by using the chromosome of E. coli strain ECOS 9-5 as the template and using the primer combination of AraCF and AraWR (GATATA-CATATGTTCACTCCATCCAAAAAAACGGGT; SEQ ID NO: 46). A 50 µL PCR (polymerase chain reaction) mixture contains 1×GDP-HiFi PCR buffer B, 200 µM dATP, dTTP, dGTP, and dCTP, 1 µM amplification primers, 100 ng chromosome of ECOS 9-5, and 1U GDP-HiFi DNA polymerase. The condition of the PCR reaction was 96° C. for 5 minutes (1 step); 94° C. for 30 seconds, 55° C. for 30 seconds, 68° C. for 1 minutes (35 cycles); 68° C. for 5 minutes (1 step). The PCR product was recovered by PCR-M™ Clean Up system and ligated into pJET1.2 plasmid with T4 DNA ligase, and the plasmid was named pJET-ARABW after confirming the correct sequence by DNA sequencing. After that, pJET-ARABW was cleaved with EcoRI and NdeI, and the DNA fragment containing araC and araB-W expression element was recovered by using Gel-M™ gel extraction system kit (GMbiolab, Taiwan). The DNA fragment containing araC and araB-W expression element was ligated into pRPSJ-GFPT with the same restriction enzyme cleavage by using T4 DNA ligase. The adhesive product was transformed into E. coli ECOS 9-5. The transformants were screened by colony polymerase chain reaction, and the plasmids of transformants were extracted for DNA sequencing. The plasmid with correct sequences was named pARABW-GFPT.

2. Construction of Expression Vectors with Modified Ribosome Binding Sites

The chromosome of E. coli strain ECOS 9-5 was used as the template, and primer AraCF was used with primers AraM1R, AraM2R, AraM3R, AraM4R, and AraM5R, respectively, to modify the sequence of the ribosome binding site. A 50 µL PCR mixture contains 1×GDP-HiFi PCR buffer B, 200 µM dATP, dTTP, dGTP, and dCTP, 1 µM amplification primers, 100 ng chromosome of ECOS 9-5, and 1U GDP-HiFi DNA polymerase. The condition of the PCR reaction was 96° C. for 5 minutes (1 step); 94° C. for 30 seconds, 55° C. for 30 seconds, 68° C. for 1 minutes (35 cycles); 68° C. for 5 minutes (1 step). The PCR products were recovered by PCR-M™ Clean Up system and ligated into pJET1.2 plasmid with T4 DNA ligase, and a total of five plasmids were named pJET-ARABM1, pJET-ARABM2, pJET-ARABM3, pJET-ARABM4, and pJET-ARABM5, respectively, after confirming the correct sequences by DNA sequencing. After that, each of the five plasmids was respectively cleaved with EcoRI and NdeI, and the DNA fragments containing araC and araB-M1, araC and araB-M2, araC and araB-M3, araC and araB-M4, araC and araB-M5 expression elements were recovered by using Gel-M™ gel extraction system kit (GMbiolab, Taiwan). These five expression elements were individually ligated into pRPSJ-GFPT with the same restriction enzyme cleavage by using T4 DNA ligase. The adhesive product was transformed into *E. coli* ECOS 9-5. The transformants were screened by colony polymerase chain reaction, and the plasmids of transformants were extracted for DNA sequencing. The plasmids with correct sequences were named pARABM1-GFPT, pARABM2-GFPT, pARABM3-GFPT, pARABM4-GFPT, and pARABM5-GFPT, respectively.

3. Construction of an Expression Vector with Modified −10 Region of the Promoter and Ribosome Binding Site The plasmid pARABM4-GFPT was used as the template, and the primer combinations of AraCF/AraM6-2 and AraM6-1/GFPSALIR were used, respectively, to amplify DNA fragments. A 50 μL PCR mixture contains 1×GDP-HiFi PCR buffer B, 200 μM dATP, dTTP, dGTP, and dCTP, 1 μM amplification primers, 100 ng pARABM4-GFPT, and 1U GDP-HiFi DNA polymerase. The condition of the PCR reaction was 96° C. for 2 minutes (1 step); 94° C. for 30 seconds, 55° C. for 30 seconds, 68° C. for 1 minutes (35 cycles); 68° C. for 5 minutes (1 step). After the PCR reaction, whether the DNA fragments with anticipated size exist or not was checked by agarose gel electrophoresis. The PCR products were recovered by Gel-M™ gel extraction system kit. After that, the two recovered PCR products were used as the templates, and the primer combination of AraCF/GFPSALIR was used to amplify a DNA fragment. The condition of the PCR reaction was 98° C. for 2 minutes (1 step); 94° C. for 30 seconds, 55° C. for 30 seconds, 68° C. for 1 minutes (35 cycles); 68° C. for 5 minutes (1 step). After this step, the DNA fragment containing araC and araB-M6 expression element was obtained. The PCR product was recovered with PCR-M™ Clean Up system and ligated into pJET1.2 plasmid with T4 DNA ligase, and a plasmid was named pJET-ARABM6 after confirming the correct sequences by DNA sequencing. After that, the plasmid pJET-ARABM6 was cleaved with EcoRI and NdeI, and the DNA fragment containing araC and araB-M6 expression element was recovered by using Gel-M™ gel extraction system kit. The DNA fragment containing araC and araB-M6 expression element was ligated into pRPSJ-GFPT with the same restriction enzyme cleavage by using T4 DNA ligase. The adhesive product was transformed into *E. coli* ECOS 9-5. The transformants were screened by colony polymerase chain reaction, and the plasmids were extracted for DNA sequencing. The plasmid with correct sequences was named pARABM6-GFPT.

4. Construction of an Expression Vector with Modified −16 Region of the Promoter and Ribosome Binding Site The plasmid pARABM4-GFPT was used as the template, and the primer combinations of AraCF/AraM7-2 and AraM7-1/GFPSALIR were used, respectively, to amplify DNA fragments. A 50 μL PCR mixture contains 1×GDP-HiFi PCR buffer B, 200 μM dATP, dTTP, dGTP, and dCTP, 1 μM amplification primers, 100 ng pARABM4-GFPT, and 1U GDP-HiFi DNA polymerase. The condition of the PCR reaction was 96° C. for 2 minutes (1 step); 94° C. for 30 seconds, 55° C. for 30 seconds, 68° C. for 1 minutes (35 cycles); 68° C. for 5 minutes (1 step). After the PCR reaction, whether the DNA fragments with anticipated size exist or not were checked by agarose gel electrophoresis. The PCR products were recovered by Gel-M™ gel extraction system kit. After that, the two recovered PCR products were used as the templates, and the primer combination of AraCF/GFPSALIR was used to amplify a DNA fragment. The condition of the PCR reaction was 96° C. for 2 minutes (1 step); 94° C. for 30 seconds, 55° C. for 30 seconds, 68° C. for 1 minutes (35 cycles); 68° C. for 5 minutes (1 step). After this step, the araC and araB-M7 expression element were obtained. The PCR product was recovered with PCR-M™ Clean Up system and ligated into pJET1.2 plasmid with T4 DNA ligase, and a plasmid was named pJET-ARABM7 after confirming the correct sequences by DNA sequencing. After that, the plasmid pJET-ARABM7 was cleaved with EcoRI and NdeI, and the DNA fragment containing araC and araB-M7 expression element was recovered by using Gel-M™ gel extraction system kit. The DNA fragment containing araC and araB-M7 expression element was ligated into pRPSJ-GFPT with the same restriction enzyme cleavage by using T4 DNA ligase. The adhesive product was transformed into *E. coli* ECOS 9-5. The transformants were screened by colony polymerase chain reaction, and the plasmids of transformants were extracted for DNA sequencing. The plasmid with correct sequences was named pARABM7-GFPT.

5. Construction of an Expression Vector with Modified Ribosome Binding Site and Bacteriophage T7 Epsilon Enhancer Sequence The chromosome of *E. coli* strain ECOS 9-5 was used as the template, and the primer AraCF in combination with primer AraM10R was used to modify expression elements. A 50 μL PCR mixture contains 1×GDP-HiFi PCR buffer B, 200 μM dATP, dTTP, dGTP, and dCTP, 1 μM amplification primers, 100 ng chromosome of ECOS 9-5, and 1U GDP-HiFi DNA polymerase. The condition of the PCR reaction was 96° C. for 5 minutes (1 step); 94° C. for 30 seconds, 55° C. for 30 seconds, 68° C. for 1 minutes (35 cycles); 68° C. for 5 minutes (1 step). The PCR product was recovered by PCR-M™ Clean Up system and ligated into pJET1.2 plasmid with T4 DNA ligase, and the plasmid was named pJET-ARABM10 after confirming the correct sequence by DNA sequencing. After that, pJET-ARABM10 was cleaved with EcoRI and NdeI, and the DNA fragments containing araC and araB-M10 expression element was recovered by using Gel-M™ gel extraction system kit. The DNA fragment containing araC and araB-M10 expression element were ligated into pRPSJ-GFPT with the same restriction enzyme cleavage by using T4 DNA ligase. The adhesive product was transformed into *E. coli* ECOS 9-5. The transformants were screened by colony polymerase chain reaction, and the plasmids of transformants were extracted for DNA sequencing. The plasmid with correct sequences was named pARABM10-GFPT.

6. Construction of an Expression Vectors with Modified −16 Region of the Promoter, Ribosome Binding Site, and Bacteriophage T7 Epsilon Enhancer Sequence The pARABM7-GFPT was used as the template, and the primer combination of AraCF/AraM10R was used to amplify DNA fragments. A 50 μL PCR mixture contains 1×GDP-HiFi PCR buffer B, 200 μM dATP, dTTP, dGTP, and dCTP, 1 μM amplification primers, 100 ng pARABM7-GFPT, and 1U GDP-HiFi DNA polymerase. The condition of the PCR reaction was 96° C. for 2 minutes (1 step); 94° C. for 30 seconds, 55° C. for 30 seconds, 68° C. for 1 minutes (35 cycles); 68° C. for 5 minutes (1 step). After the PCR reaction, whether the DNA fragment with anticipated size exist or not was checked by agarose gel electrophoresis. The PCR product was recovered by Gel-M™ gel extraction system kit and ligated into pJET1.2 plasmid with T4 DNA ligase, and the plasmid was named pJET-ARABM11 after confirming the correct sequence by DNA sequencing. After that, pJET-ARABM11 was cleaved with EcoRI and NdeI, and the DNA fragment containing araC and araB-M11 expression element was recovered by using Gel-M™ gel extraction system kit. The DNA fragment containing araC and araB-M11 expression element was ligated into pRPSJ-GFPT with the same restriction enzyme cleavage by using T4 DNA ligase. The adhesive product was transformed into E. coli ECOS 9-5. The transformants were screened by colony polymerase chain reaction, and the plasmids of transformants were extracted for DNA sequencing. The plasmid with correct sequences was named pARABM11-GFPT.

7. Construction of Expression Vectors with Additional Downstream Sequences

Primers were designed for different downstream sequences, and DNA amplification was performed by polymerase chain reaction. The plasmid pARABM7-GFPT was used as the template, and different primer combinations were used to amplify DNA fragments. A 50 μL PCR mixture contains 1×GDP-HiFi PCR buffer B, 200 μM dATP, dTTP, dGTP, and dCTP, 1 μM primers for amplification, 100 ng pARABM7-GFPT, and 1U GDP-HiFi DNA polymerase. The condition of the PCR reaction was 96° C. for 2 minutes (1 step); 94° C. for 30 seconds, 55° C. for 30 seconds, 68° C. for 30 seconds (35 cycles); 68° C. for 5 minutes (1 step). After the PCR reaction, whether the DNA fragments with anticipated size exist or not were checked by agarose gel electrophoresis. Four PCR products were recovered by Gel-M™ gel extraction system kit and then cleaved with NdeI and SalI. The PCR products cleaved with restriction enzyme were recovered by PCR-M™ Clean Up system, and the four DNA fragments containing downstream sequences and a green fluorescent protein gene were ligated into pARABM7-GFPT and pARABM11-GFPT plasmids with the same restriction enzyme cleavage by using T4 DNA ligase, respectively. The adhesive products were transformed into E. coli ECOS 9-5. The transformants were screened by colony polymerase chain reaction, and the plasmids of transformants were extracted for DNA sequencing. The resulting plasmids derived from pARABM7-GFPT with correct sequences were named pARABM7-DS1GFPT, pARABM7-DS2GFPT, pARABM7-DS4GFPT, and pARABM7-DS5GFPT, respectively. The resulting plasmids derived from pARABM11-GFPT with correct sequences were named pARABM11-DS1GFPT, pARABM11-DS2GFPT, pARABM11-DS4GFPT, and pARABM11-DS5GFPT, respectively.

Primer pairs used in the above-mentioned experimental procedures are listed in the following table.

TABLE 2 the sequences of the primers used in the present invention

| Primers | SEQ ID NO: | Primer Sequence (5' to 3') |
| --- | --- | --- |
| AraCF | SEQ ID NO: 30 | CAATATGAATTCGCATAATGTGCCTGTCAAATGGAC |
| AraM1R | SEQ ID NO: 31 | GATATACATATGTATACCTCCTTAATCCAAAAAAACGGGTATGGAGAAAC |
| AraM2R | SEQ ID NO: 32 | GATATACATATGTATACCTCCTTTATCCAAAAAAACGGGTATGGAGAAAC |
| AraM3R | SEQ ID NO: 33 | GATATACATATGTATACCTCCTATATCCAAAAAAACGGGTATGGAGAAAC |
| AraM4R | SEQ ID NO: 34 | GATATACATATGTATTCCTCCTATATCCAAAAAAACGGGTATGGAGAAAC |
| AraM5R | SEQ ID NO: 35 | GATATACATATGTATATCTCCTTCATCCAAAAAAACGGGTATGGAGAAAC |
| AraM6-1 | SEQ ID NO: 36 | CCTGACGCTTTTTATCGCAACTCTCTATAATTTCTCCATACCC |
| AraM6-2 | SEQ ID NO: 37 | GGGTATGGAGAAATTATAGAGAGTTGCGATAAAAAGCGTCAGG |
| GFPSALIR | SEQ ID NO: 38 | TAGATAGTCGACTTATTTGTAAAGCTCATCCATG |
| AraM7-1 | SEQ ID NO: 39 | CGCTTTTTATCGCAACTTGCTACTGTTTCTCCATACC |
| AraM7-2 | SEQ ID NO: 40 | GGTATGGAGAAACAGTAGCAAGTTGCGATAAAAAGCG |
| AraM10R | SEQ ID NO: 41 | GATATACATATGTATTCCTCCTTCTTAAAGTTAAACAAAAAAACGGGTATGGAGAAACAG |
| DS1F | SEQ ID NO: 42 | GATATACATATGCACACACACACACACACACTCAGGTACCCCAGATCTGGGTACCCTGG |
| DS2F | SEQ ID NO: 43 | GATATACATATGAAAGCAATTTTCGTAGGTACCCCAGATCTGGGTACCCTGG |
| DS4F | SEQ ID NO: 44 | GATATACATATGAATCACAAAGTGGGTACCCCAGATCTGGGTACCCTGG |
| DS5F | SEQ ID NO: 45 | GATATACATATGACTAGCAAAAGAGGTACCCCAGATCTGGGTACCCTGG |

Example 2: Analysis of the Arabinose-Inducible Expression Vectors of the Present Invention In this example, the arabinose-inducible expression vectors obtained in Example 1 were transformed into E. coli (ECOS 9-5), and protein (GFP) expression was induced. Then, the fluorescence intensity was measured with a microplate reader to estimate the difference of the expression levels between the expression elements of Example 1 and the original expression element.

1. Induction of Transformants with Arabinose-Inducible Expression Vector and Determination of Fluorescence Intensity The E. coli ECOS 9-5 transformants were inoculated into LB medium containing tetracycline (25 μg/mL) and incubated in the condition of 37° C., 180 rpm. After overnight incubation, the bacterial culture was inoculated into LB medium containing tetracycline (25 μg/mL) at a ratio of 1:20 and incubated in the condition of 37° C., 180 rpm. Bacteria were cultured to about $OD_{600}$ of 0.4 measured by a spectrophotometer, and 0.2% arabinose was added for induction of protein expression. After 4 hours of induction, the cells of bacteria were collected by centrifugation (20630×g, 5 min, at 4° C.) and then washed with 1 mL PBS buffer. The cells of bacteria were collected by centrifugation (20630×g, 5 min, at 4° C.) and then suspended in 1 mL PBS buffer. The absorbance of 100 μL bacterial culture was measured at a wavelength of 600 nm using a TECAN INFINITE M200 microplate reader. The fluorescence intensity of the sample was also measured at an excitation wavelength of 482 nm and an emission wavelength of 512 nm. Fluorescence intensity is presented as the fluorescence value per unit cell (fluorescence/$OD_{600}$). The experimental results are shown in Table 3 and Table 4.

TABLE 3

Expression efficiency of the original expression element and the expression elements of the present invention

| Expression | Fluorescence intensity (Fluorescence/$OD_{600}$) | |
|---|---|---|
| elements | Non-induced | Induced |
| araB-W | 159 | 24101 |
| araB-M1 | 201 | 33414 |
| araB-M2 | 174 | 34187 |
| araB-M3 | 171 | 35160 |
| araB-M4 | 172 | 51582 |
| araB-M5 | 186 | 42569 |
| araB-M6 | 2088 | 82371 |
| araB-M7 | 802 | 69239 |
| araB-M10 | 226 | 55353 |
| araB-M11 | 777 | 75043 |

TABLE 4

Effects of different downstream sequences on the expression efficiency of different expression elements

| Expression | Fluorescence intensity (Fluorescence/$OD_{600}$) | |
|---|---|---|
| elements | Non-induced | Induced |
| araB-W | 241 | 21402 |
| araB-M7 | 1142 | 83474 |
| araB-M7-DS1 | 1010 | 77141 |
| araB-M7-DS2 | 940 | 40848 |
| araB-M7-DS4 | 988 | 87211 |
| araB-M7-DS5 | 942 | 82315 |
| araB-M11 | 954 | 85652 |
| araB-M11-DS1 | 1347 | 71286 |
| araB-M11-DS2 | 1090 | 34847 |
| araB-M11-DS4 | 1227 | 81543 |
| araB-M11-DS5 | 1034 | 84833 |

Expression elements araB-M1, araB-M2, araB-M3, araB-M4, and araB-M5 with modified ribosome binding sites were compared. Based on the experimental data, the above-mentioned five expression elements all significantly improve the expression level of the gene to be expressed in comparison with the original expression element. Among these expression elements, the expression level of the gene to be expressed by using araB-M4 is 2.14 times higher than that of the original expression element.

Next, the araB-M6 and araB-M7 expression elements with modified −10 or −16 region of promoter, respectively were compared with the original expression element. Based on the experimental data, the expression level of the gene to be expressed by using araB-M6 is 3.42 times higher than that of the original expression element, and the expression level of the gene to be expressed by using araB-M7 is 2.87 times higher than that of the original expression element. It is noteworthy that the data of araB-M6 and araB-M7 expression elements are 1.6 and 1.34 times higher than the data of araB-M4 expression element, respectively, which means the modified −10 or −16 region of the promoter combining with the modified ribosome binding site has additive effects.

The araB-M10 and araB-M4 expression elements with bacteriophage T7 epsilon enhancer sequences were compared with the original expression element. It is noted that the expression level by using araB-M10 is 1.07 times higher than the expression level by using araB-M4 and 2.3 times higher than the expression level by using the original expression element. In addition, the araB-M11 and araB-M7 expression elements with bacteriophage T7 epsilon enhancer sequences were compared with the original expression element. It is noted that the expression level by using araB-M11 is 1.08 times higher than the expression level by using araB-M7 and 3.11 times higher than the expression level by using the original expression element. The data shows that the addition of bacteriophage T7 epsilon enhancer sequences has positive effects on expression level.

As shown in Table 3, the eight expression elements constructed by different downstream sequences which were added at the downstream of the start codons of araB-M7 and araB-M11, respectively, were compared with the original expression element. It is noted that the expression efficiency of araB-M7-DS4 is 1.04 times higher than that of araB-M7, and 4.07 times higher than that of the original expression element. In addition, the expression efficiencies of other expression elements are improved comparing to that of the original expression element.

What is claimed is:

1. An expression element for an arabinose-inducible expression system, comprising: a promoter and at least one of the following elements:
   a ribosome binding site having a sequence of SEQ ID NO: 02; or a bacteriophage T7 epsilon enhancer element having a sequence of SEQ ID NO: 08;
   wherein −16 region of the promoter has a sequence of SEQ ID NO: 07.

2. The expression element of claim 1, wherein −10 region of the promoter has a sequence of SEQ ID NO: 06.

3. The expression element of claim 1, which has a sequence of SEQ ID NO: 19 or SEQ ID NO: 21.

4. An expression cassette, comprising: the expression element of claim 1, a start codon, a gene to be expressed, and a stop codon.

5. The expression cassette of claim 4, wherein −10 region of the promoter of the expression element has a sequence of SEQ ID NO: 06.

6. The expression cassette of claim 4, wherein a downstream sequence is disposed between the start codon and the gene to be expressed, and the downstream sequence has a sequence of SEQ ID NO: 09, SEQ ID NO: 10, SEQ ID NO: 11, SEQ ID NO: 12, or a combination thereof.

7. The expression cassette of claim 4, wherein the expression element has a sequence of SEQ ID NO: 19, or SEQ ID NO: 21.

8. The expression cassette of claim 4, further comprising a regulatory gene.

9. The expression cassette of claim 8, wherein the regulatory gene is araC of arabinose-inducible expression system.

10. The expression cassette of claim 4, wherein the gene to be expressed is a gene encoding a green fluorescent protein, a gene encoding an enzyme, a gene encoding an antigen, a gene encoding a peptide or a protein having physiological activity, or a combination thereof.

11. A vector, comprising: the expression cassette of claim 4 and a multiple cloning site.

12. The vector of claim 11, wherein −10 region of the promoter of the expression element of the expression cassette has a sequence of SEQ ID NO: 06.

13. The vector of claim 11, wherein a downstream sequence is disposed between the start codon and the gene to be expressed of the expression cassette, and the downstream sequence has a sequence of SEQ ID NO: 09, SEQ ID NO: 10, SEQ ID NO: 11, SEQ ID NO: 12, or a combination thereof.

14. The vector of claim 11, wherein the expression element of the expression cassette has a sequence of SEQ ID NO: 19 or SEQ ID NO: 21.

15. The vector of claim 11, further comprising a replication start site, a selectable marker, a signal peptide, or a combination thereof.

16. The vector of claim 15, wherein the selectable marker is a drug resistance selectable marker, a non-drug resistance selectable marker, or a combination thereof.

* * * * *

SEQUENCE LISTING

<160> NUMBER OF SEQ ID NOS: 46

<210> SEQ ID NO 1
<211> LENGTH: 5
<212> TYPE: DNA
<213> ORGANISM: Artificial Sequence
<220> FEATURE:
<223> OTHER INFORMATION: modified Shine-Dalgarno sequence

<400> SEQUENCE: 1 aggag                                                                    5

<210> SEQ ID NO 2
<211> LENGTH: 6
<212> TYPE: DNA
<213> ORGANISM: Artificial Sequence
<220> FEATURE:
<223> OTHER INFORMATION: modified Shine-Dalgarno sequence

<400> SEQUENCE: 2 aggagg                                                                          6

<210> SEQ ID NO 3
<211> LENGTH: 7
<212> TYPE: DNA
<213> ORGANISM: Artificial Sequence
<220> FEATURE:
<223> OTHER INFORMATION: modified Shine-Dalgarno sequence

<400> SEQUENCE: 3 aggaggt                                                                         7

<210> SEQ ID NO 4
<211> LENGTH: 8
<212> TYPE: DNA
<213> ORGANISM: Artificial Sequence
<220> FEATURE:
<223> OTHER INFORMATION: modified Shine-Dalgarno sequence

<400> SEQUENCE: 4 aaggaggt                                                                        8

<210> SEQ ID NO 5
<211> LENGTH: 9
<212> TYPE: DNA
<213> ORGANISM: Artificial Sequence
<220> FEATURE:
<223> OTHER INFORMATION: modified Shine-Dalgarno sequence

<400> SEQUENCE: 5 taaggaggt                                                                       9

<210> SEQ ID NO 6
<211> LENGTH: 6
<212> TYPE: DNA
<213> ORGANISM: Artificial Sequence
<220> FEATURE:
<223> OTHER INFORMATION: modified promoter

<400> SEQUENCE: 6 tataat                                                                          6

<210> SEQ ID NO 7
<211> LENGTH: 2
<212> TYPE: DNA
<213> ORGANISM: Artificial Sequence
<220> FEATURE:
<223> OTHER INFORMATION: modified promoter

<400> SEQUENCE: 7 tg                                                                              2

<210> SEQ ID NO 8
<211> LENGTH: 10
<212> TYPE: DNA
<213> ORGANISM: Artificial Sequence
<220> FEATURE:
<223> OTHER INFORMATION: modified T7 epsilon

<400> SEQUENCE: 8
tttaacttta                                                                     10

<210> SEQ ID NO 9
<211> LENGTH: 27
<212> TYPE: DNA

<213> ORGANISM: Artificial Sequence
<220> FEATURE:
<223> OTHER INFORMATION: downstream sequence

<400> SEQUENCE: 9
atgcacacac acacacacac acactca         27

<210> SEQ ID NO 10
<211> LENGTH: 18
<212> TYPE: DNA
<213> ORGANISM: Artificial Sequence
<220> FEATURE:
<223> OTHER INFORMATION: downstream sequence

<400> SEQUENCE: 10
atgaaagcaa ttttcgta         18

<210> SEQ ID NO 11
<211> LENGTH: 15
<212> TYPE: DNA
<213> ORGANISM: Artificial Sequence
<220> FEATURE:
<223> OTHER INFORMATION: downstream sequence

<400> SEQUENCE: 11
atgaatcaca aagtg         15

<210> SEQ ID NO 12
<211> LENGTH: 15
<212> TYPE: DNA
<213> ORGANISM: Artificial Sequence
<220> FEATURE:
<223> OTHER INFORMATION: downstream sequence

<400> SEQUENCE: 12
atgactagca aaaga         15

<210> SEQ ID NO 13
<211> LENGTH: 81
<212> TYPE: DNA
<213> ORGANISM: Artificial Sequence
<220> FEATURE:
<223> OTHER INFORMATION: expression cassette

<400> SEQUENCE: 13
ggatcctacc tgacgctttt tatcgcaact ctctactgtt tctccatacc cgttttttg         60 gattaaggag gtatacatat g         81

<210> SEQ ID NO 14
<211> LENGTH: 81
<212> TYPE: DNA
<213> ORGANISM: Artificial Sequence
<220> FEATURE:
<223> OTHER INFORMATION: expression cassette

<400> SEQUENCE: 14
ggatcctacc tgacgctttt tatcgcaact ctctactgtt tctccatacc cgttttttg         60 gataaaggag gtatacatat g         81

<210> SEQ ID NO 15
<211> LENGTH: 81
<212> TYPE: DNA
<213> ORGANISM: Artificial Sequence
<220> FEATURE:
<223> OTHER INFORMATION: expression cassette -continued

```
<400> SEQUENCE: 15
ggatcctacc tgacgctttt tatcgcaact ctctactgtt tctccatacc cgttttttttg     60 gatataggag gtatacatat g                                                 81

<210> SEQ ID NO 16
<211> LENGTH: 81
<212> TYPE: DNA
<213> ORGANISM: Artificial Sequence
<220> FEATURE:
<223> OTHER INFORMATION: expression cassette

<400> SEQUENCE: 16
ggatcctacc tgacgctttt tatcgcaact ctctactgtt tctccatacc cgttttttttg     60 gatataggag gaatacatat g                                                 81

<210> SEQ ID NO 17
<211> LENGTH: 81
<212> TYPE: DNA
<213> ORGANISM: Artificial Sequence
<220> FEATURE:
<223> OTHER INFORMATION: expression cassette

<400> SEQUENCE: 17
ggatcctacc tgacgctttt tatcgcaact ctctactgtt tctccatacc cgttttttttg     60 gatgaaggag atatacatat g                                                 81

<210> SEQ ID NO 18
<211> LENGTH: 81
<212> TYPE: DNA
<213> ORGANISM: Artificial Sequence
<220> FEATURE:
<223> OTHER INFORMATION: expression cassette

<400> SEQUENCE: 18
ggatcctacc tgacgctttt tatcgcaact ctctataatt tctccatacc cgttttttttg     60 gatataggag gaatacatat g                                                 81

<210> SEQ ID NO 19
<211> LENGTH: 81
<212> TYPE: DNA
<213> ORGANISM: Artificial Sequence
<220> FEATURE:
<223> OTHER INFORMATION: expression cassette

<400> SEQUENCE: 19
ggatcctacc tgacgctttt tatcgcaact tgctactgtt tctccatacc cgttttttttg     60 gatataggag gaatacatat g                                                 81

<210> SEQ ID NO 20
<211> LENGTH: 89
<212> TYPE: DNA
<213> ORGANISM: Artificial Sequence
<220> FEATURE:
<223> OTHER INFORMATION: expression cassette

<400> SEQUENCE: 20
ggatcctacc tgacgctttt tatcgcaact ctctactgtt tctccatacc cgttttttttg     60 tttaacttta agaaggagga atacatatg                                         89

<210> SEQ ID NO 21
```

```
<211> LENGTH: 89
<212> TYPE: DNA
<213> ORGANISM: Artificial Sequence
<220> FEATURE:
<223> OTHER INFORMATION: expression cassette

<400> SEQUENCE: 21
ggatcctacc tgacgctttt tatcgcaact tgctactgtt tctccatacc cgttttttg      60 tttaacttta agaaggagga atacatatg                                       89

<210> SEQ ID NO 22
<211> LENGTH: 105
<212> TYPE: DNA
<213> ORGANISM: Artificial Sequence
<220> FEATURE:
<223> OTHER INFORMATION: expression cassette with downstream sequence

<400> SEQUENCE: 22
ggatcctacc tgacgctttt tatcgcaact tgctactgtt tctccatacc cgttttttg      60 gatataggag gaatacatat gcacacacac acacacacac actca                     105

<210> SEQ ID NO 23
<211> LENGTH: 96
<212> TYPE: DNA
<213> ORGANISM: Artificial Sequence
<220> FEATURE:
<223> OTHER INFORMATION: expression cassette with downstream sequence

<400> SEQUENCE: 23
ggatcctacc tgacgctttt tatcgcaact tgctactgtt tctccatacc cgttttttg      60 gatataggag gaatacatat gaaagcaatt ttcgta                               96

<210> SEQ ID NO 24
<211> LENGTH: 93
<212> TYPE: DNA
<213> ORGANISM: Artificial Sequence
<220> FEATURE:
<223> OTHER INFORMATION: expression cassette with downstream sequence

<400> SEQUENCE: 24
ggatcctacc tgacgctttt tatcgcaact tgctactgtt tctccatacc cgttttttg      60 gatataggag gaatacatat gaatcacaaa gtg                                  93

<210> SEQ ID NO 25
<211> LENGTH: 93
<212> TYPE: DNA
<213> ORGANISM: Artificial Sequence
<220> FEATURE:
<223> OTHER INFORMATION: expression cassette with downstream sequence

<400> SEQUENCE: 25
ggatcctacc tgacgctttt tatcgcaact tgctactgtt tctccatacc cgttttttg      60 gatataggag gaatacatat gactagcaaa aga                                  93

<210> SEQ ID NO 26
<211> LENGTH: 113
<212> TYPE: DNA
<213> ORGANISM: Artificial Sequence
<220> FEATURE:
<223> OTHER INFORMATION: expression cassette with downstream sequence

<400> SEQUENCE: 26
ggatcctacc tgacgctttt tatcgcaact tgctactgtt tctccatacc cgttttttg      60
```
tttaacttta agaaggagga atacatatgc acacacacac acacacacac tca         113

<210> SEQ ID NO 27
<211> LENGTH: 103
<212> TYPE: DNA
<213> ORGANISM: Artificial Sequence
<220> FEATURE:
<223> OTHER INFORMATION: expression cassette with downstream sequence

<400> SEQUENCE: 27
gatcctacct gacgcttttt atcgcaactt gctactgttt ctccataccc gttttttgt    60 ttaactttaa gaaggaggaa tacatatgaa agcaatttc gta                     103

<210> SEQ ID NO 28
<211> LENGTH: 101
<212> TYPE: DNA
<213> ORGANISM: Artificial Sequence
<220> FEATURE:
<223> OTHER INFORMATION: expression cassette with downstream sequence

<400> SEQUENCE: 28
ggatcctacc tgacgctttt tatcgcaact tgctactgtt tctccatacc cgttttttg    60 tttaacttta agaaggagga atacatatga atcacaaagt g                      101

<210> SEQ ID NO 29
<211> LENGTH: 101
<212> TYPE: DNA
<213> ORGANISM: Artificial Sequence
<220> FEATURE:
<223> OTHER INFORMATION: expression cassette with downstream sequence

<400> SEQUENCE: 29
ggatcctacc tgacgctttt tatcgcaact tgctactgtt tctccatacc cgttttttg    60 tttaacttta agaaggagga atacatatga ctagcaaaag a                      101

<210> SEQ ID NO 30
<211> LENGTH: 36
<212> TYPE: DNA
<213> ORGANISM: Artificial Sequence
<220> FEATURE:
<223> OTHER INFORMATION: primer

<400> SEQUENCE: 30
caatatgaat tcgcataatg tgcctgtcaa atggac                            36

<210> SEQ ID NO 31
<211> LENGTH: 50
<212> TYPE: DNA
<213> ORGANISM: Artificial Sequence
<220> FEATURE:
<223> OTHER INFORMATION: primer

<400> SEQUENCE: 31
gatatacata tgtataccte cttaatccaa aaaaacgggt atggagaaac              50

<210> SEQ ID NO 32
<211> LENGTH: 50
<212> TYPE: DNA
<213> ORGANISM: Artificial Sequence
<220> FEATURE:
<223> OTHER INFORMATION: primer

<400> SEQUENCE: 32
gatatacata tgtataccte ctttatccaa aaaaacgggt atggagaaac                50

<210> SEQ ID NO 33
<211> LENGTH: 50
<212> TYPE: DNA
<213> ORGANISM: Artificial Sequence
<220> FEATURE:
<223> OTHER INFORMATION: primer

<400> SEQUENCE: 33
gatatacata tgtataccte ctatatccaa aaaaacgggt atggagaaac                50

<210> SEQ ID NO 34
<211> LENGTH: 50
<212> TYPE: DNA
<213> ORGANISM: Artificial Sequence
<220> FEATURE:
<223> OTHER INFORMATION: primer

<400> SEQUENCE: 34
gatatacata tgtattccte ctatatccaa aaaaacgggt atggagaaac                50

<210> SEQ ID NO 35
<211> LENGTH: 50
<212> TYPE: DNA
<213> ORGANISM: Artificial Sequence
<220> FEATURE:
<223> OTHER INFORMATION: primer

<400> SEQUENCE: 35
gatatacata tgtatatctc cttcatccaa aaaaacgggt atggagaaac                50

<210> SEQ ID NO 36
<211> LENGTH: 43
<212> TYPE: DNA
<213> ORGANISM: Artificial Sequence
<220> FEATURE:
<223> OTHER INFORMATION: primer

<400> SEQUENCE: 36
cctgacgctt tttatcgcaa ctctctataa tttctccata ccc                       43

<210> SEQ ID NO 37
<211> LENGTH: 43
<212> TYPE: DNA
<213> ORGANISM: Artificial Sequence
<220> FEATURE:
<223> OTHER INFORMATION: primer

<400> SEQUENCE: 37
gggtatggag aaattataga gagttgcgat aaaaagcgtc agg                       43

<210> SEQ ID NO 38
<211> LENGTH: 34
<212> TYPE: DNA
<213> ORGANISM: Artificial Sequence
<220> FEATURE:
<223> OTHER INFORMATION: primer

<400> SEQUENCE: 38
tagatagtcg acttatttgt aaagctcatc catg                                 34

<210> SEQ ID NO 39
<211> LENGTH: 37
<212> TYPE: DNA
<213> ORGANISM: Artificial Sequence

```
<220> FEATURE:
<223> OTHER INFORMATION: primer

<400> SEQUENCE: 39 cgcttttat cgcaacttgc tactgtttct ccatacc                              37

<210> SEQ ID NO 40
<211> LENGTH: 37
<212> TYPE: DNA
<213> ORGANISM: Artificial Sequence
<220> FEATURE:
<223> OTHER INFORMATION: primer

<400> SEQUENCE: 40
ggtatggaga acagtagca agttgcgata aaaagcg                              37

<210> SEQ ID NO 41
<211> LENGTH: 60
<212> TYPE: DNA
<213> ORGANISM: Artificial Sequence
<220> FEATURE:
<223> OTHER INFORMATION: primer

<400> SEQUENCE: 41
gatatacata tgtattcctc cttcttaaag ttaaacaaaa aaacgggtat ggagaaacag    60

<210> SEQ ID NO 42
<211> LENGTH: 61
<212> TYPE: DNA
<213> ORGANISM: Artificial Sequence
<220> FEATURE:
<223> OTHER INFORMATION: primer

<400> SEQUENCE: 42
gatatacata tgcacacaca cacacacaca cactcaggta ccccagatct gggtaccctg    60
g                                                                    61

<210> SEQ ID NO 43
<211> LENGTH: 52
<212> TYPE: DNA
<213> ORGANISM: Artificial Sequence
<220> FEATURE:
<223> OTHER INFORMATION: primer

<400> SEQUENCE: 43
gatatacata tgaaagcaat tttcgtaggt accccagatc tgggtaccct gg            52

<210> SEQ ID NO 44
<211> LENGTH: 49
<212> TYPE: DNA
<213> ORGANISM: Artificial Sequence
<220> FEATURE:
<223> OTHER INFORMATION: primer

<400> SEQUENCE: 44
gatatacata tgaatcacaa agtgggtacc ccagatctgg gtaccctgg                49

<210> SEQ ID NO 45
<211> LENGTH: 49
<212> TYPE: DNA
<213> ORGANISM: Artificial Sequence
<220> FEATURE:
<223> OTHER INFORMATION: primer

<400> SEQUENCE: 45
```

```
gatatacata tgactagcaa aagaggtacc ccagatctgg gtaccctgg                49

<210> SEQ ID NO 46
<211> LENGTH: 36
<212> TYPE: DNA
<213> ORGANISM: Artificial Sequence
<220> FEATURE:
<223> OTHER INFORMATION: primer

<400> SEQUENCE: 46
gatatacata tgttcactcc atccaaaaaa acgggt                              36
```